(12) United States Patent
Williams

(10) Patent No.: US 10,607,461 B2
(45) Date of Patent: Mar. 31, 2020

(54) DRONE BASED SECURITY SYSTEM

(71) Applicant: Albert Williams, Commerce, CA (US)

(72) Inventor: Albert Williams, Commerce, CA (US)

( * ) Notice: Subject to any disclaimer, the term of this patent is extended or adjusted under 35 U.S.C. 154(b) by 0 days.

(21) Appl. No.: 15/884,830

(22) Filed: Jan. 31, 2018

(65) Prior Publication Data

US 2018/0233007 A1    Aug. 16, 2018

Related U.S. Application Data

(60) Provisional application No. 62/452,842, filed on Jan. 31, 2017.

(51) Int. Cl.
| | | |
|---|---|---|
| *G08B 13/196* | (2006.01) | |
| *A61K 31/519* | (2006.01) | |
| *A61K 45/06* | (2006.01) | |
| *A61P 13/12* | (2006.01) | |
| *A61K 31/55* | (2006.01) | |
| *B64C 39/02* | (2006.01) | |
| *H04N 7/18* | (2006.01) | |
| *A61K 31/4365* | (2006.01) | |
| *A61K 38/095* | (2019.01) | |

(52) U.S. Cl.
CPC .......... *G08B 13/196* (2013.01); *A61K 31/519* (2013.01); *A61K 31/55* (2013.01); *A61K 45/06* (2013.01); *A61P 13/12* (2018.01); *B64C 39/024* (2013.01); *H04N 7/185* (2013.01); *A61K 31/4365* (2013.01); *A61K 38/095* (2019.01); *B64C 2201/127* (2013.01)

(58) Field of Classification Search
CPC ....... A61P 13/12; A61K 31/519; A61K 45/06; B64C 39/024; B64C 2201/127; G08B 13/196; H04N 7/185
See application file for complete search history.

(56) References Cited

U.S. PATENT DOCUMENTS

| | | | |
|---|---|---|---|
| 6,965,816 B2 * | 11/2005 | Walker | B64C 13/20 244/189 |
| 7,302,316 B2 | 11/2007 | Beard et al. | |
| 8,511,606 B1 | 8/2013 | Lutke et al. | |
| 8,768,555 B2 | 7/2014 | Duggan et al. | |
| 8,964,298 B2 * | 2/2015 | Haddick | G06F 3/013 359/630 |
| 9,044,543 B2 * | 6/2015 | Levien | G05D 1/00 |
| 9,061,102 B2 * | 6/2015 | Levien | G05D 1/0011 |
| 9,193,458 B2 * | 11/2015 | Pongratz | B64C 37/02 |
| 9,373,014 B1 * | 6/2016 | Mehranfar | G05D 1/104 |
| 9,494,936 B2 * | 11/2016 | Kerzner | G05D 1/0022 |
| 9,505,494 B1 * | 11/2016 | Marlow | B64C 39/024 |
| 9,540,102 B2 * | 1/2017 | Levien | B64C 39/024 |
| 9,552,736 B2 * | 1/2017 | Taveira | G05D 1/102 |
| 9,601,022 B2 * | 3/2017 | Taveira | G08G 5/006 |

(Continued)

FOREIGN PATENT DOCUMENTS

CN    105208348 A    12/2015

*Primary Examiner* — Philip P. Dang
(74) *Attorney, Agent, or Firm* — Avyno Law P.C.

(57) ABSTRACT

A drone security system with at least a drone and a drone base having been setup with locations that are part of a tradition security systems and where the traditional security system is in communication with drone base enabling the drone to respond to events that occur in the traditional security system and for the drone to also follow a predetermined path with checkpoints.

18 Claims, 11 Drawing Sheets

(56) References Cited

U.S. PATENT DOCUMENTS

| | | | |
|---|---|---|---|
| 9,915,945 B2* | 3/2018 | Fox | G01S 19/51 |
| 10,040,552 B2* | 8/2018 | Gordon | B64C 39/024 |
| 10,118,698 B2* | 11/2018 | Zerick | H04W 4/029 |
| 2014/0303814 A1 | 10/2014 | Burema et al. | |
| 2014/0344118 A1 | 11/2014 | Parpia et al. | |
| 2014/0354402 A1* | 12/2014 | Joao | G07C 9/00571 |
| | | | 340/5.52 |
| 2015/0025788 A1* | 1/2015 | Crain | G01S 5/02 |
| | | | 701/400 |
| 2015/0235540 A1* | 8/2015 | Verna | H04L 67/26 |
| | | | 340/539.11 |
| 2016/0054737 A1 | 2/2016 | Soll et al. | |
| 2016/0127641 A1* | 5/2016 | Gove | G06T 1/0007 |
| | | | 348/143 |
| 2016/0144959 A1* | 5/2016 | Meffert | B64C 39/024 |
| | | | 701/3 |
| 2016/0214715 A1* | 7/2016 | Meffert | B64C 39/024 |
| 2016/0266579 A1* | 9/2016 | Chen | B64C 39/024 |
| 2016/0370800 A1* | 12/2016 | Chau | G05D 1/0088 |
| 2017/0092109 A1* | 3/2017 | Trundle | G08B 25/006 |
| 2017/0092138 A1* | 3/2017 | Trundle | B64C 39/024 |
| 2017/0195568 A1* | 7/2017 | Leizerovich, Jr. | |
| | | | H04N 5/23238 |
| 2017/0199979 A1* | 7/2017 | Reiner | G16H 50/30 |
| 2017/0219676 A1* | 8/2017 | Tran | H04W 12/02 |
| 2017/0225801 A1* | 8/2017 | Bennett | B64F 1/222 |
| 2017/0227965 A1* | 8/2017 | Decenzo | H04L 67/025 |
| 2017/0237484 A1* | 8/2017 | Heath | H04Q 11/0066 |
| | | | 398/26 |
| 2017/0330466 A1* | 11/2017 | Demetriades | G08G 5/0034 |
| 2018/0035136 A1* | 2/2018 | Crowe | H04N 21/21805 |
| 2018/0109767 A1* | 4/2018 | Li | H04N 5/23206 |
| 2018/0139152 A1* | 5/2018 | Shaw | H04W 84/18 |

* cited by examiner

DRONE BASED SECURITY SYSTEM

I. CROSS-REFERENCE TO RELATED APPLICATIONS

This application claims priority to U.S. Provisional application 62/452,842, titled Drone Based Security System, by Albert Williams, filed on Jan. 31, 2017, which is incorporated by reference herein.

II. FIELD OF INVENTION

The invention relates to a security system and, in particular, a drone based security system.

III. BACKGROUND

The invention relates to a security system and, in particular, a drone based security system. Security is important in today's society. It is very crucial to protect people, loved ones and/or their property. Technological advances in security systems continues to be important in protecting society against theft, robberies, crimes and attacks. While certain technology can be used to prevent crime, current technologies and other means for monitoring and preventing crime have limitations. More practical solutions are needed for today's security systems.

Security systems are generally of two types: security guards and monitoring systems—both of which have extreme limitations. Real-time monitoring by security guards is costly. Security guards have limitations on where they can travel, how fast they can respond to particular situations and how far and how fast they can pursue criminal activity.

Monitoring systems can record activity, alert owners and responders of unusual activity and trigger alarms; however, such systems cannot track activity, follow objects or perform other functions that may be performed by live security surveillance.

One solution to the current limitations of security systems is to utilize unmanned aerial vehicle technology to improve security. However, the use of unmanned aerial vehicles must rely on manually operated drones. Manually operated drones have problems that include the need for a person to be present to control the flight pattern of the drone, to physically gather the drone, to physically connect the drone to a power source and to manually observe the drone to prevent it from crashing. A human drone operator can also be costly. Accordingly, a need exists for an automated security system capable of performing functions not able to be performed by live security guards, electronic monitoring and alarm systems, manually operated drones and/or a combination of any of the foregoing.

III. SUMMARY OF THE INVENTION

No existing security systems utilize pre-programmed, fully automated drones to perform monitoring, alerting or other security or surveillance tasks. There are significant differences between what drones can do and what existing security systems can do. A guard will stop following an object but a drone will not. A guard does not record video and audio or carry an alarm but a drone does. The drone has a large advantage in the view it has over its surrounding area.

The pre-programmed, fully automated drone of the present invention also solves many problems that occur with manually operated drones. For example, the automatic drone may be programmed to follow a pre-determined flight path at predetermined or random time intervals, return to its base without manual instruction, connect to a power source upon landing in the base for charging, sense obstacles and avoid them during flight, and provide lower operating costs than manually operated drones.

Further, the security drone of the present invention may be used from many types of applications, including both commercial and residential applications. For example, a farmer can use the drone to perform security over his/her agriculture, a home owner can use the security drone to protect his house while on vacation or out of the home, and the drone can further be used for security at a construction site, or for building security, to name a few examples.

In operation, the security drone of the present invention replaces the traditional security guard, or in some cases, for extra security measures, can be used in conjunction with a security guard. The advantages of the security drone are that it provides continuous live video and audio feed and recordings, quicker reaction time to alerts, and reduced costs over traditional security guards. It also reduces the risks placed on a security guard when responding to the threat. Further, the property owner or end user can be made aware of the circumstances surrounding an event in real-time because the security drone can instantly be deployed from the base in response to activation of one of the components of the existing security system. Generally, a drone can reach a security breach or respond to an alert much quicker than a security guard can travel on the ground to respond. The likelihood of recording crucial activity and following breach events and/or intruders is greater with an automated drone than with a standard security system or security guard.

Other devices, apparatus, systems, methods, features and advantages of the invention are or will become apparent to one with skill in the art upon examination of the following figures and detailed description. It is intended that all such additional systems, methods, features and advantages be included within this description, be within the scope of the invention, and be protected by the accompanying claims.

IV. DESCRIPTION OF FIGURES

The invention may be better understood by referring to the following figures. The components in the figures are not necessarily to scale, emphasis instead being placed upon illustrating the principles of the invention.

IV. DETAILED DESCRIPTION OF THE INVENTION

A pre-programed, automated drone based security system is provided that may be used in connection with a variety of commercial and residential applications. As will be explained further below, the security drone of the present invention may perform a variety of automated functions, be programmed to follow a pre-determined flight path at pre-determined or random time intervals, return to its base without manual instruction, connect to a power source upon landing in the base for charging and sense obstacles and avoid them during flight, among other things.

Figure 1:
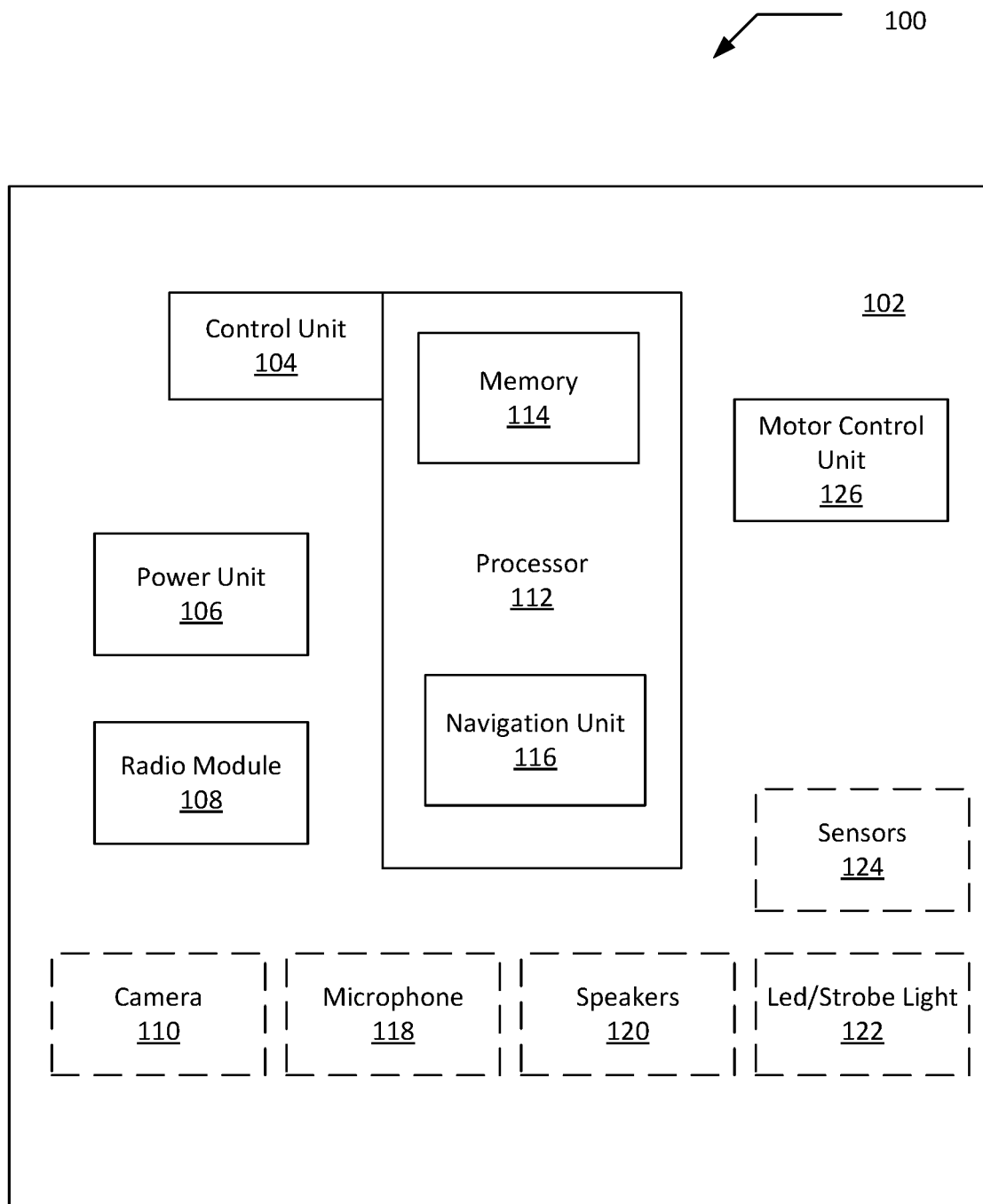
FIG. 1 illustrates a block diagram of one example of components of a drone designed in accordance with an example implementation of the invention.

In FIG. 1, an illustration of a block diagram 100 of one example of components of a drone 102 is depicted in accordance with an example implementation of the invention. As illustrated, the drone 102 includes a control unit 104, which may include a processor 112, a radio module 108, and a power unit 106. The processor 112 may include a memory 114 and a navigation unit (such as a GPS receiver), and sufficient processing power to conduct various control and computing operations for controlling the drone 102 and drone subsystems. The processor 112 may be powered from a power unit 106, such as a battery. The processor 112 may be configured with processor-executable instructions (stored in memory 114) to control the charging of the power unit from a remote source, such as by executing a charging control algorithm using a charge control circuit associated with the power unit 106. Alternatively or additionally, the power unit 106 may be configured to manage charging independent of the processor 112. The processor 112 may be coupled to a motor control unit 126 that is configured to manage the motors that drive the rotors.

Through control of the individual motors of the rotors on the drone, the drone may be controlled in flight. The processor 112 may receive input from the navigation unit 116 to determine its present position and orientation, including the position of a landing point. In some implementations, the navigation unit 116 may be equipped to navigate using GPS/GNSS signals. Alternatively or in addition, the navigation unit 116 may be equipped to navigate by receiving beacon signals or other signals from radio nodes, such as WiFi access points.

The navigation unit 116 may obtain location information associated with the WiFi access points without actually establishing a communication link with the WiFi access point. A gyro/accelerometer unit may also be provided to generate relative position information about the three dimensional orientation and movement of the drone 102 and may be used to supplement positional information to facilitate navigation independent of or in association with GPS/GNSS receiver.

The processor 112 may communicate wirelessly with a device, such as a smart phone, computer, tablet, or drone base, through a radio module. The processor 112 may also communicate with a network node, such as a WiFi access point or hotspot, a cellular network infrastructure component, or a server. Communications may be direct or through intermediate communication links, such as one or more network nodes or other communication devices. The radio module 108 may be configured to switch between cellular and WiFi connections and even maintain multiple connections. Further, bi-directional wireless communications may be established between transmit/receive antenna of the radio module 108 in the drone 102 and a transmit/receive antenna of the other communication device. The drone 102 may also include a GPS/GNSS receiver 116 configured to receive GNSS signals from positioning satellites and determine geographic coordinates from those signals. The radio module 108 may further be coupled to the navigation unit 116 and configured to receive navigation signals, such as beacon signals from an aviation navigation facility, and provide such signals to the processor 112 to assist in drone navigation.

The drone 102 may be implemented within a variety of environments in communication networks, such as private networks between devices, public networks between devices, or combinations of private and public networks. A drone may travel large distances over varying terrain including roadways. Therefore, drone mobility may require communications to be maintained while the drone is travelling to and from a destination.

While the various components coupled to the control unit 104 are shown as separate components, it is also possible for at least some of the components such as the processor, the motor control unit, the radio module, and possibly other units, to be integrated together in a single device or chip.

Other components may also be included in the drone 102 for use in the connection with the security drone of the present invention. Such other components include, but are not limited to, the following: (1) infrared and visible light camera 110; (2) microphone 118; (3) speakers 120; (4) LED flashlight/LED strobe light 122; and/or (6) altitude/other sensors 124.

Figure 2:
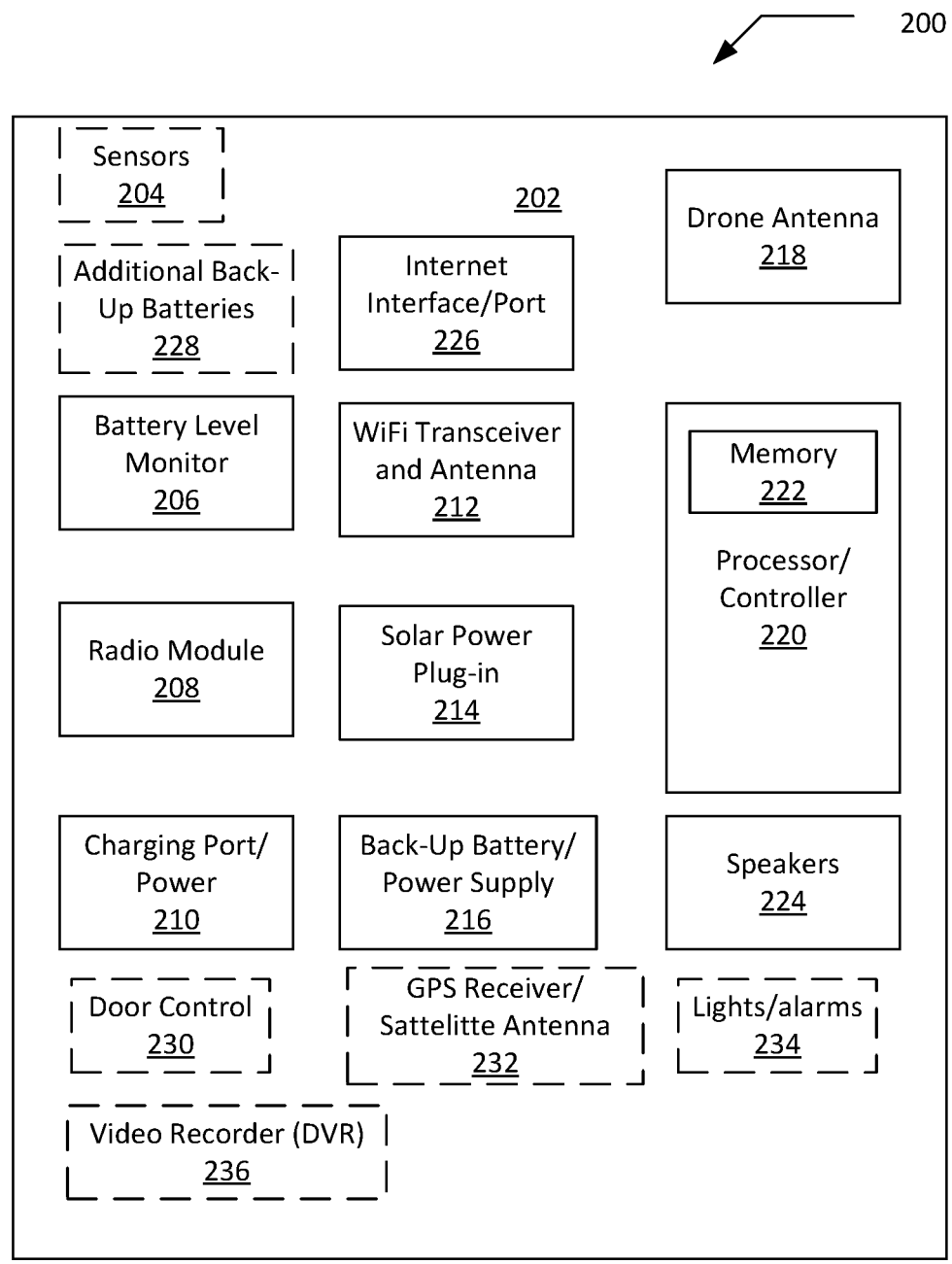
FIG. 2 illustrates a block diagram of example of components of a base for powering, storing and communicating with a drone designed in accordance with an example implementation of the invention.

Turning to FIG. 2, a block diagram 200 of example of components of a drone base 202 for powering, storing and communicating with a drone 102 is depicted in accordance with an example implementation of the invention. Elements of the drone base 202 include the charging port/power 210, battery level monitor 206, solar power plugin port 214, power supply with backup battery 216, drone antennae 218, WiFi transceiver and antennae 212, internet interface/port 226, processor/controller 220 with memory 222 storing instructions and operating system, audio content, and speakers 224. Optional elements of the base include additional heavy duty back-up batteries 228, wind speed, humidity, and/or other sensors 204, door control 230, GPS receiver/satellite antennae 232, alarms and strobe light, and video recorder such as a digital video recorder (DVR) 236. For a communication hub, the system may use a local or, optionally, a cloud based server in communication with the base, the drone or both.

The base may operate as the central data processor of the building security system. It can also be the charging station for the drone 102 and the communication hub between the end user (i.e. smart device used by an end user) and the drone 102. Drone instructions and audio may be digitized and uploaded to the memory 222. The internet and power connections are made with the base using standard cabled internet, WiFi, 4G, or similar internet communication approaches. The end user can monitor activity and send commands to the base 202 and drone 102 using an internet connected device, such as a computer or smart device.

Certain components, like motions and wind sensors 204, alarms/strobe lights 234 provide security to the drone base 202 and are optional. For example, the motion sensors 204 may detect when the drone base 202 is moved. The drone base 202 will optionally turn on an alarm sound and strobe light in the event of detected motion of the drone base 202. The drone base 202 may then alert a smart device in the control of the end user of detected motion activity of drone base 202.

The drone base 202 may perform the following functions:
Monitors level of drone batteries.
Shuts off charging when drone batteries are full.
Monitors main power supply.
Alerts end user of disruption in main power supply to base.
Connects base to batteries in event of loss of main power supply.
Alerts end user of decision to connect to base batteries.
Monitors battery level of base batteries.
Alerts end user that base battery level is low.
Connects solar panels to charge base batteries.
Alerts end user of decision to connect solar panels to base batteries.
Monitors health of base and drone batteries.
Alerts end user of poor battery health.
Monitors wind speed.
Commands drone to return to crater in event of high wind speed.
Monitors humidity sensors.
Commands drone to return to crater in event of snow/rain.
Alert end user of decision to return drone/prevent from launch due to severe weather conditions.
Commands base doors to open and close during drone launch and return.
Alert end user of door malfunction.
Commands drone to not launch in event of base door jam.
Commands drone to land at secondary location in event of bade door jam.
Monitors connection to WiFi, cell tower, satellite, drone and signal strength.
Commands base to connect to alternate internet in event of signal loss.
Alerts end user of decision to connect to alternate internet connection.
Commands drone to fly closer to base in event of poor communication signal.
Commands drone to change flight path.
Transmits manual operation commands to drone.
Transmits drone camera data to built-in DVR, external DVR, or cloud server.
Transmits drone audio data to built-in DVR, external DVR, or cloud server.
Transmits prerecorded audio to drone.
Receives live audio from drone.
Transmits live audio to drone.
Analyzes drone camera data for suspicious objects.
Commands drone to take a predetermined action in response to suspicious object.
Commands drone to turn on strobe light.
Commands drone to play preselected audio stored on drone.
Commands drone to follow suspicious object within a geo fence.
Alerts end user of suspicious object detection.
Receives drone sensor data.
Analyzes drone sensor data.
Monitors Ethernet internet connection.
Alerts end user of malfunction of any base hardware.
Integrates with security access panel, burglar, fire, and access control systems.
Alerts end user in event of motion activity detected by building system.
Commands drone to fly to location of detected motion activity.
Monitors base heat and motion sensors.
Commands base alert sound and strobe light to turn on in event of detected heat or motion activity near base.
Commands drone to launch, observe, and record detected heat or motion activity near base.
Alerts end user of detected heat or motion activity near base.

Setup of the security drone system (drone 102 and drone base 202) involves identifying a GPS location for each component or element (windows, doors, gates, fire alarms, cameras, motion sensors etc.) of the existing security, fire, and access control systems. Security task commands originate from the end user through the interface and from the existing security systems.

When one of the components of the existing security system is activated, it sends a command to the security drone 102/security drone base 202. The security drone 102 leaves the drone base 202, or its predetermined flight path, and flies to the GPS coordinates of the activated component. The drone 102 records video and audio of the component and transmits a live feed to the smart device or computer of the end user.

The drone 102 sends a notification to the smart device/computer through one or more of the interfaces. The drone 102 continues to record video and audio of the component until the end user commands the drone to return to base, perform another security task, or the drone 102 runs low on battery in which case it will automatically return to the drone base 202.

Figure 3:
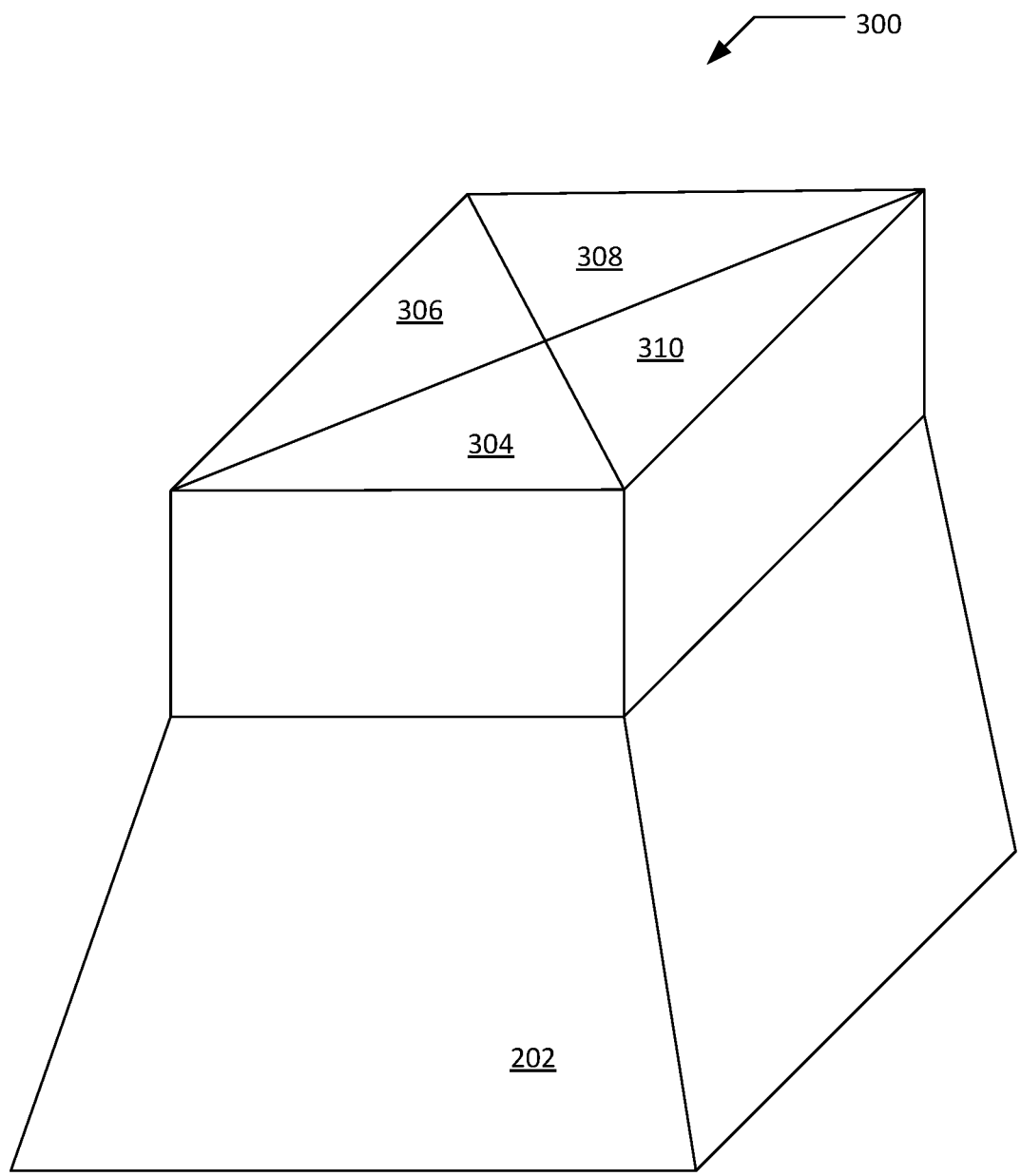
FIG. 3 is a diagram of the drone base of FIG. 2 with a plurality of doors 306-310 in accordance with an example implementation.

In FIG. 3, a diagram 300 of the drone base 202 of FIG. 2 with a plurality of doors 306-310 is depicted in accordance with an example implementation. The drone base 202 with a plurality of doors to house and charge the drone 102 is depicted with the doors 304-308 being closable in order to protect the drone 102 from the elements and animals. In an example embodiment, the drone 102 can descend into the drone base 202. The inside of the base may be shaped like a cone. At the bottom of the cone, wheels may be located in the walls to guide the drone and give it freedom to fly out of the base. The base charging port is at the bottom of the cone. When the drone 102 lands in the drone base 202, the charging port of the power unit 106 on the drone 102 automatically connects to the charging port/power 210 in the drone base 202. When the drone 102 descends into the drone base 202, the entire body of the drone may be housed beneath the rim of the drone base 202. In other implementations, the drone 102 may attach to a drone base without being enclosed by the drone base 202. In yet other implementations, the drone 102 may be locked or securely clamped or connected to the drone base 202 while connected to the base. The processor/controller 220 of the drone base 202 may control the clamps.

Further, drone base doors 304-310 are an optional component. When provided, they open and close to allow the drone 102 to be contained within the drone base 202 and to exit the drone base 202. The drone base 202 can command the doors 304-310 to open and close during the launch and return of the drone 102 in response to the processor/controller 220. The drone base 202 can alert a smart device associated with the end user of doors 304-310 malfunction and can provide a signal to the drone 102 to not launch. The drone base 202 can further command the drone 102 to land at a secondary location or secondary drone base.

Figure 4:
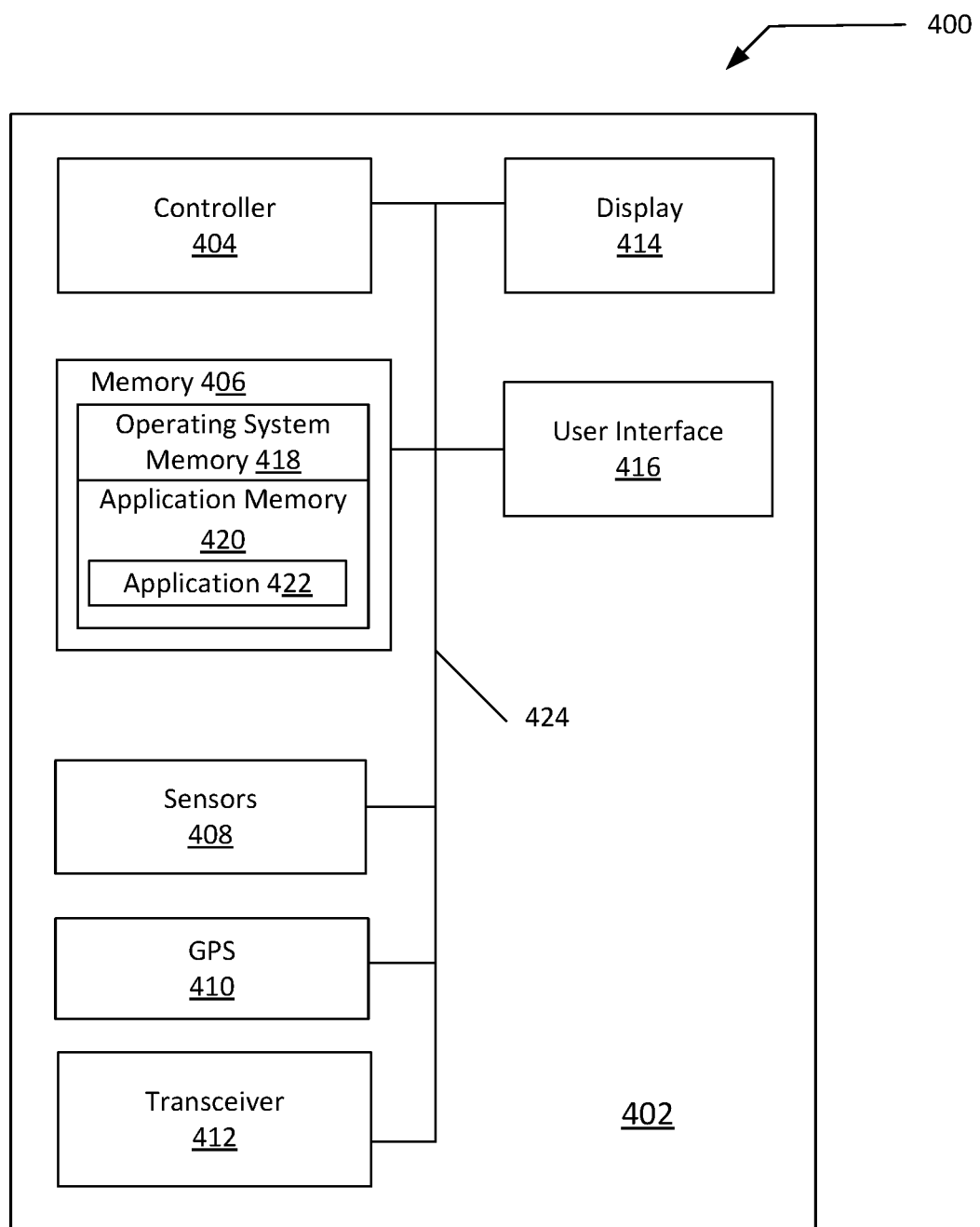
FIG. 4 illustrates a block diagram of a smart device in accordance with an example implementation of the invention.

Turning to FIG. 4, an illustration 400 a block diagram of a smart device in accordance with and example implementation of the invention. A controller 104 is coupled to a memory 106, sensors 108, GPS receiver 110, transceiver 112, display 114, and user interface 416 by communication and electrical bus 424. The controller 404 executes a plurality of instructions stored in operating system memory 418 that operates smart device 402. The instructions for a drone control application are stored in application memory 420 and executed by controller 404. In response to the instructions, the user interface 416 accepts input for the user, display 414 displays results and notifies the user of information that is needed. Sensors 408 may include sensors that detect temperature, wind speed, altitude, etc. GPS receiver 410 receives location data and may also determine speed, direction, and altitude of the drone along with changes in speed, direction and altitude. The transceiver 412 enables the smart device to communicate via WiFi/Bluetooth/cellular (i.e. 3G, 4G, GSM) with a network or cloud.

Figure 5:
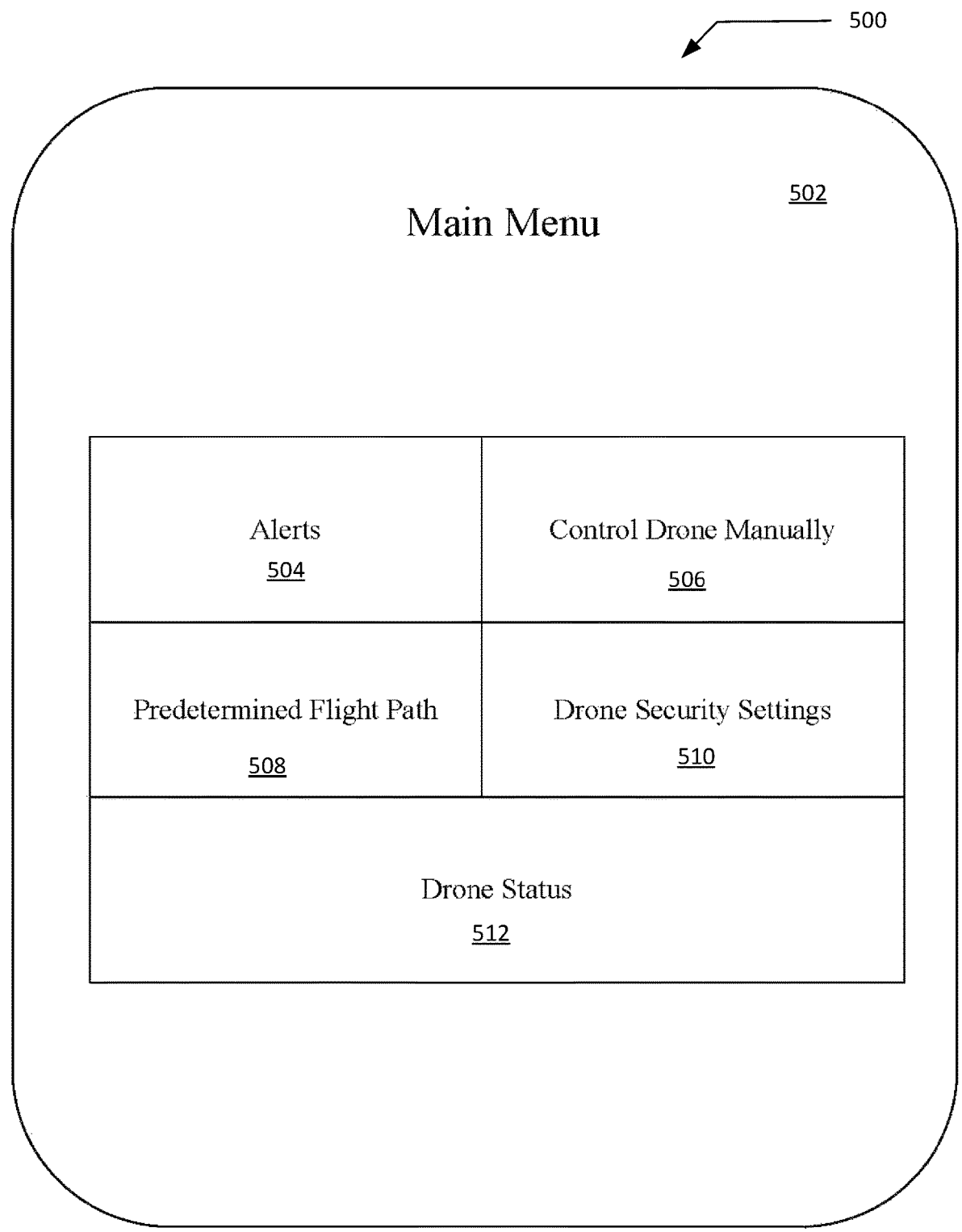
FIG. 5 illustrates a graphical user interface displayed on the smart device of FIG. 4 in accordance with an example implementation of the invention.

In FIG. 5, an illustration 500 of a graphical user interface (GUI) 502 displayed on the smart device 402 of FIG. 4 is depicted in accordance with and example implementation of the invention. The graphical user interface 502 is a main menu for controlling the drone security system (drone 102 and drone base 202). At the main menu 502, a user is able to select alerts 504, control drone manually 506, predetermined flight path 508, drone security settings 510, and drone status 512.

Figure 6:
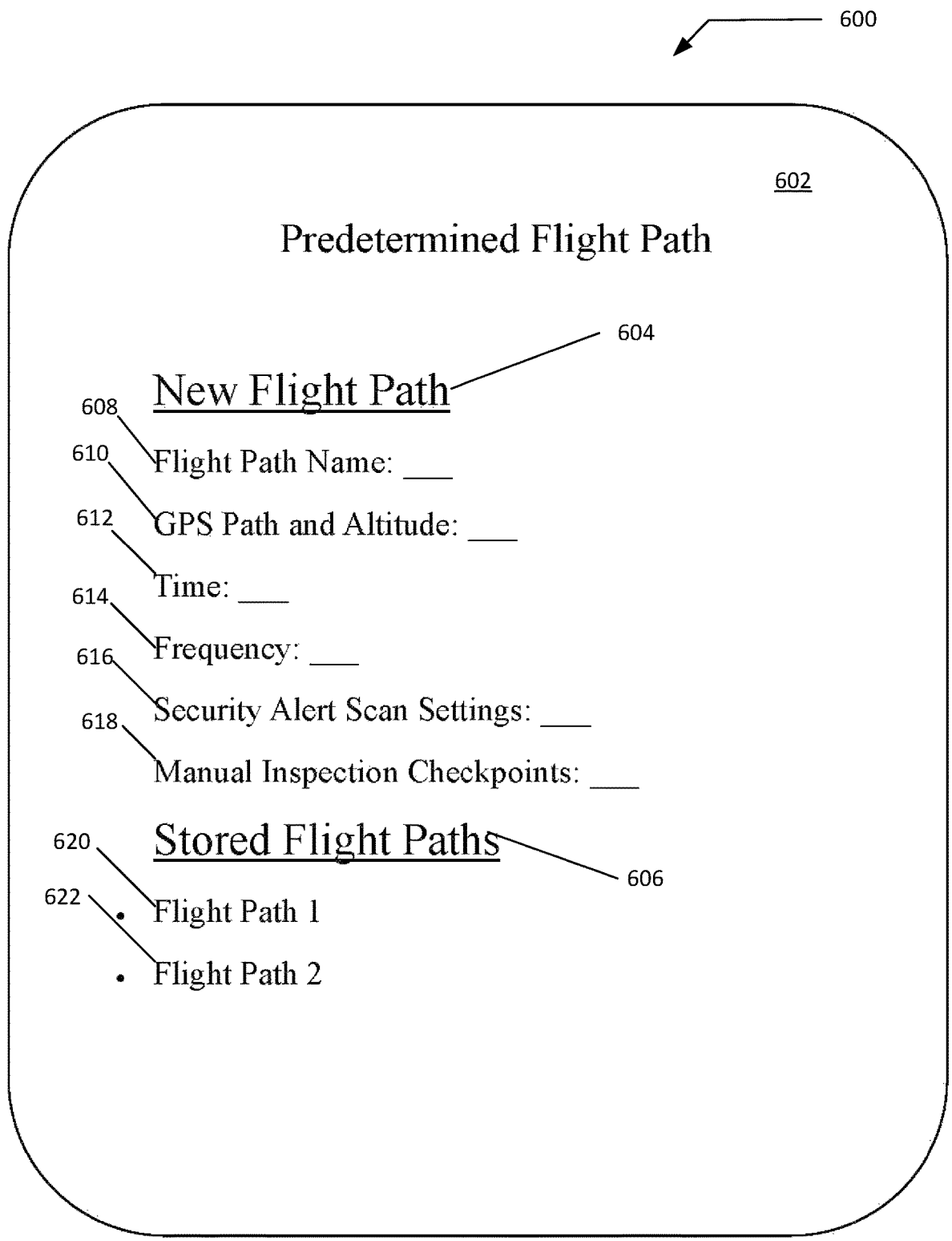
FIG. 6 illustrates a graphical user interface displayed on a smart device of FIG. 4 for setting a predetermined flight path in accordance with an example implementation of the invention.

In FIG. 6, an illustration 600 of a GUI 602 displayed on a smart device 402 of FIG. 4 for setting a predetermined flight path is depicted in accordance with an example implementation. A GPS defined flight path is defined by a user and assigned an identifier. In the predetermined flight path GUI 602, a new flight path 604 for drone 102 may be defined. The new flight path name 608 is entered, the identifier of the GPS defined flight path an altitude for the flight path are entered 610. A time period 612 for the execution of the flight path is entered along with the frequency 614 of flights during the time period. A level of security alert scan 616 is set (indicating the level of alert that the drone system must be at to trigger the flight path). Check points identified in the GPS defined flight path may be manually indicated 618 in the definition of the flight path 604 and cause the drone 102 to check those checkpoints first. Upon completion of the new flight path 604 definition, the new flight path is stored and displayed in the stored flight paths 606 list, such as "flight path 1" 620 and "flight path 2" 622. In other implementations, a confirmation button may appear prior to the storing of a new flight path 604 definition in the stored flight paths 606 list.

Figure 7:
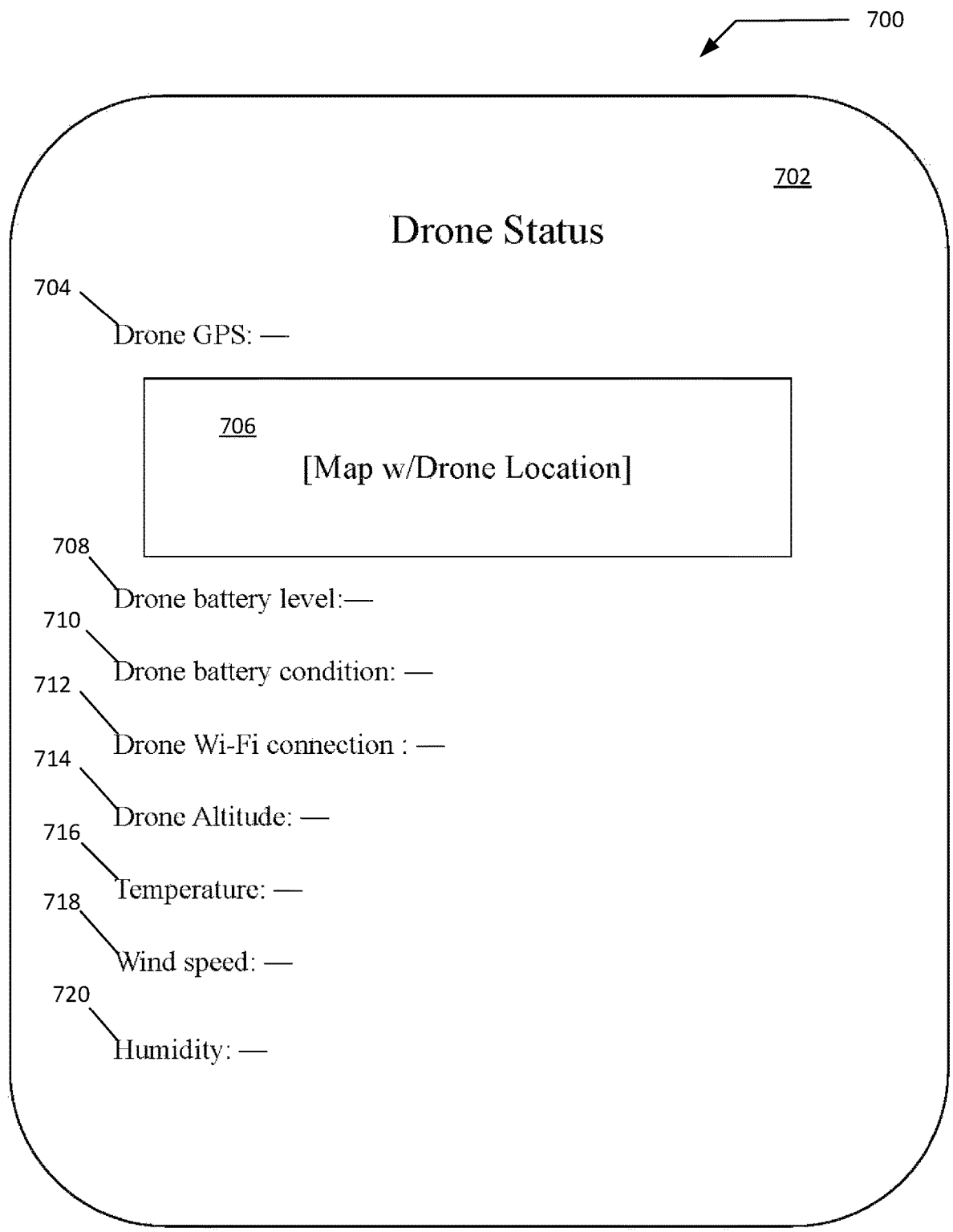
FIG. 7 illustrates a graphical user interface displayed on a smart device of FIG. 4 for monitoring the drone status in accordance with an example implementation of the invention.

Turning to FIG. 7, an illustration 700 of a GUI 702 displayed on a smart device of FIG. 4 for monitoring the drone status is depicted in accordance with an example implementation of the invention. The drone status GUI 702 displays the current GPS coordinates 704 of drone 102 and based upon drone data received from the drone 102. A map 706 may also be provided that illustrates the drone 102 location on a digital map. The map 706 may also depict other items such as structures, drone base 202, and checkpoints. In yet other implementations, digital images (such as vegetation, structures, points of interest, sensor events) may be superimposed over map 706 providing additional information. The drone battery level 708 is provided and may be displayed as volts, time before being drained, flight time remaining or a combination of battery information to give but a few examples. In other implementations, the displayed battery level may have been reduced by a safety margin to assure power for the drone 102 to successfully return to base. The safety margin may be determined by a calculation of the battery power required for the flight path from the furthest checkpoint to the drone base 202. Additional drone battery condition 710 information is displayed in GUI 702 also and may include information such as, current draw, battery condition indicator, charging status, etc.).

The current network or drone WiFi connection 712 may also be depicted in the GUI 702 and indicate the identity of the wireless network and type of security for the network. current environmental conditions such as Drone Altitude 714, temperature 716, wind speed 718, humidity 720, and other sensor data such as light, predetermined sound pitch (such as breaking glass, etc.)

Figure 8:
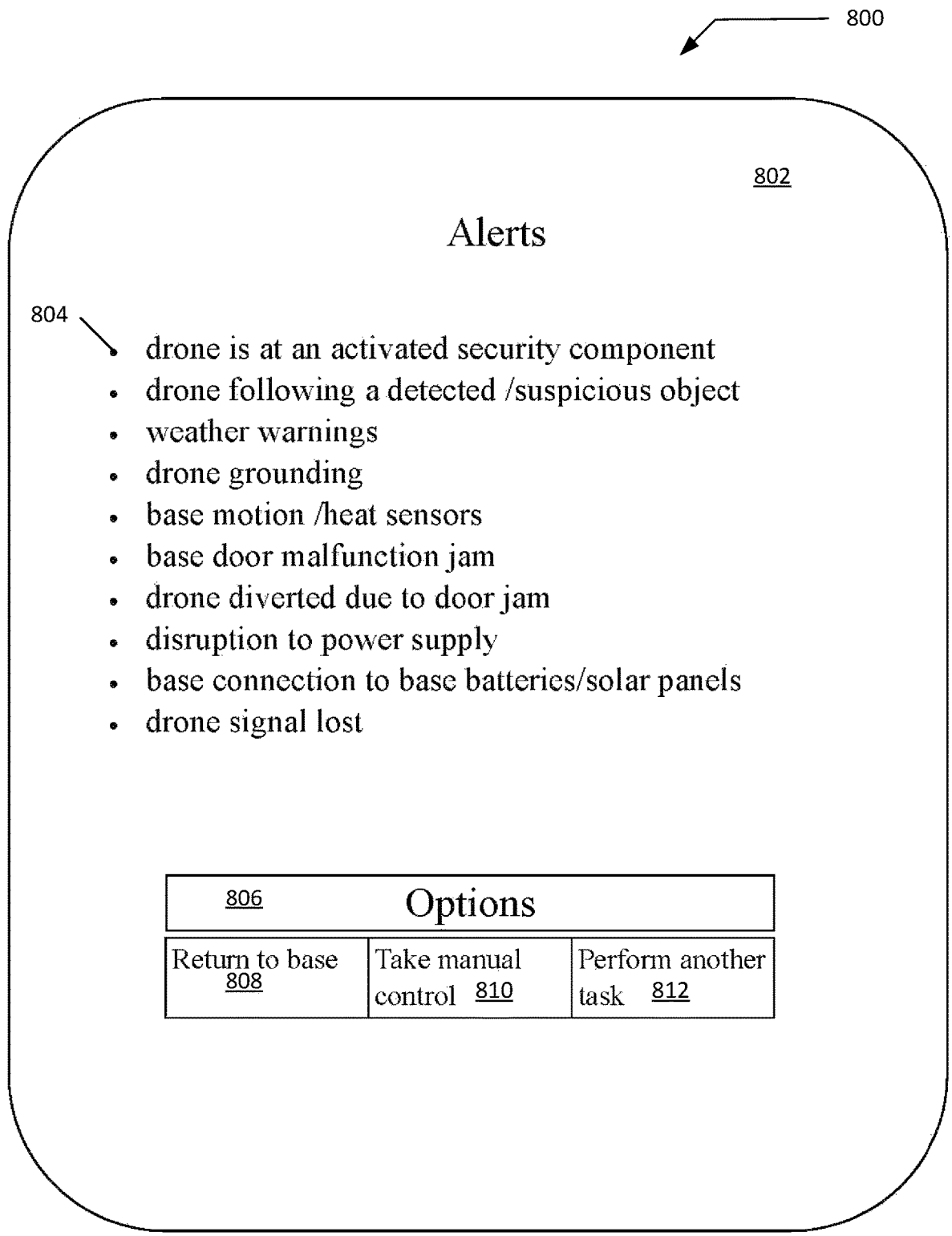
FIG. 8 illustrates a graphical user interface displayed on a smart device of FIG. 4 for alerts in accordance with an example implementation of the invention.

In FIG. 8, an illustration 800 of a GUI displayed on a smart device 402 of FIG. 4 for alerts 802 in accordance with an example implementation of the invention. The different alerts generated by the drone 102 or drone base 202 are displayed in the alerts GUI 802. Additionally, alert options 806 may be accessed to turn "on" or "off" categories of alerts. Furthermore, the drone 102 may be instructed to return to base 808, manual control GUI accessed 810 or other predefined/user defined tasks GUI accessed 812.

Figure 9:
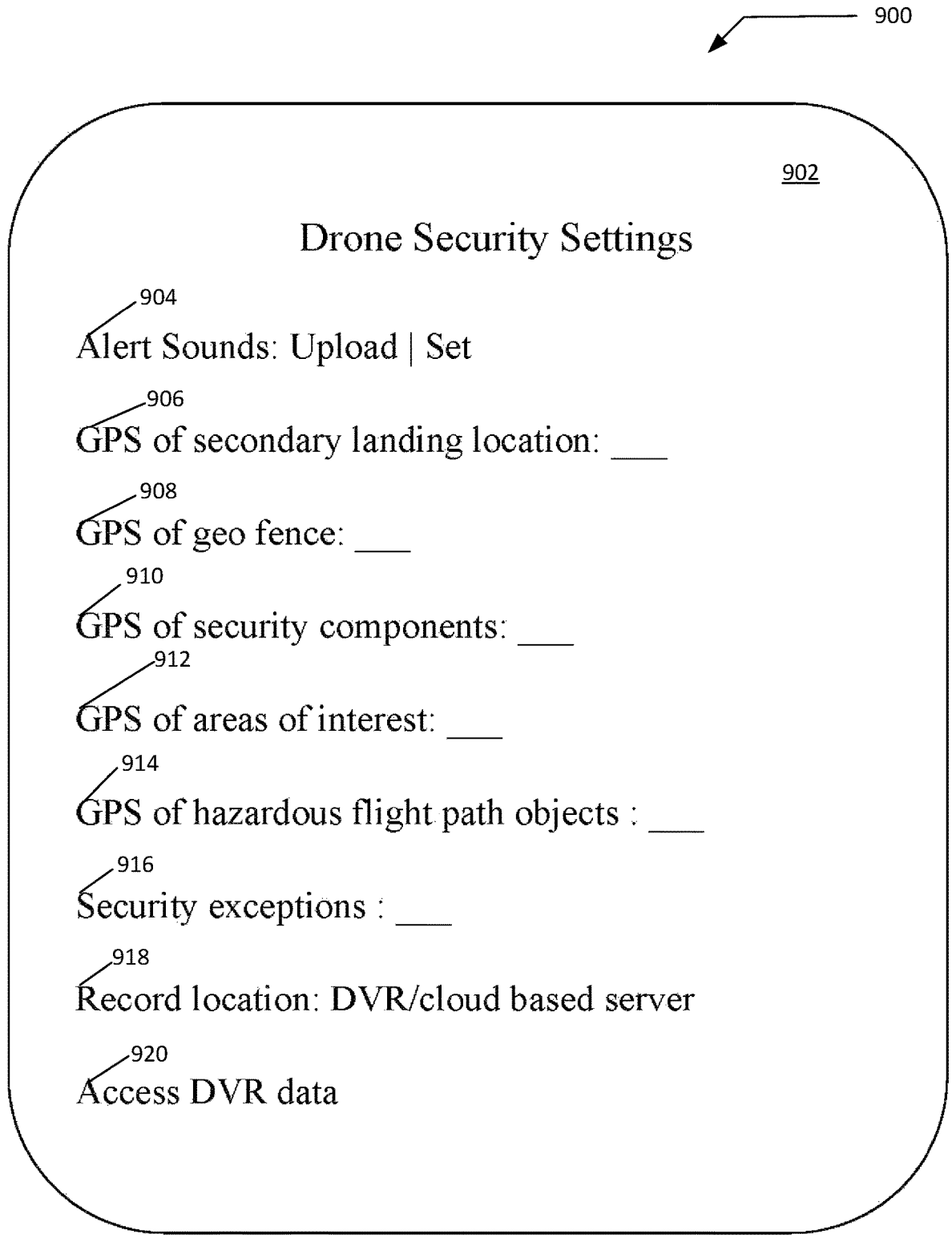
FIG. 9 illustrates a graphical user interface displayed on a smart device of FIG. 4 for the drone security settings in accordance with an example implementation of the invention.

Turning to FIG. 9, an illustration 900 of a GUI 902 displayed on a smart device 102 of FIG. 4 for the drone security settings is depicted in accordance with an example implementation of the invention. Alert sounds 904 may be uploaded and set, a GPS location of a secondary landing location 906 is identified, GPS geo fencing identifiers are selectable 908. The identifier of GPS security components 910 may also be identified. The identifier may be GPS coordinates, or in other implementations a file identifier of a file of security component locations may be identified to the drone security system. GPS location of areas of interest 912 may also be entered using the GUI 902. Further, GPS location of hazardous flight path objects may be entered at input 914. Security exceptions input 916, DVR location 918, and a button to access DVR data 920 are also available in the drone security settings GUI 902.

Figure 10:
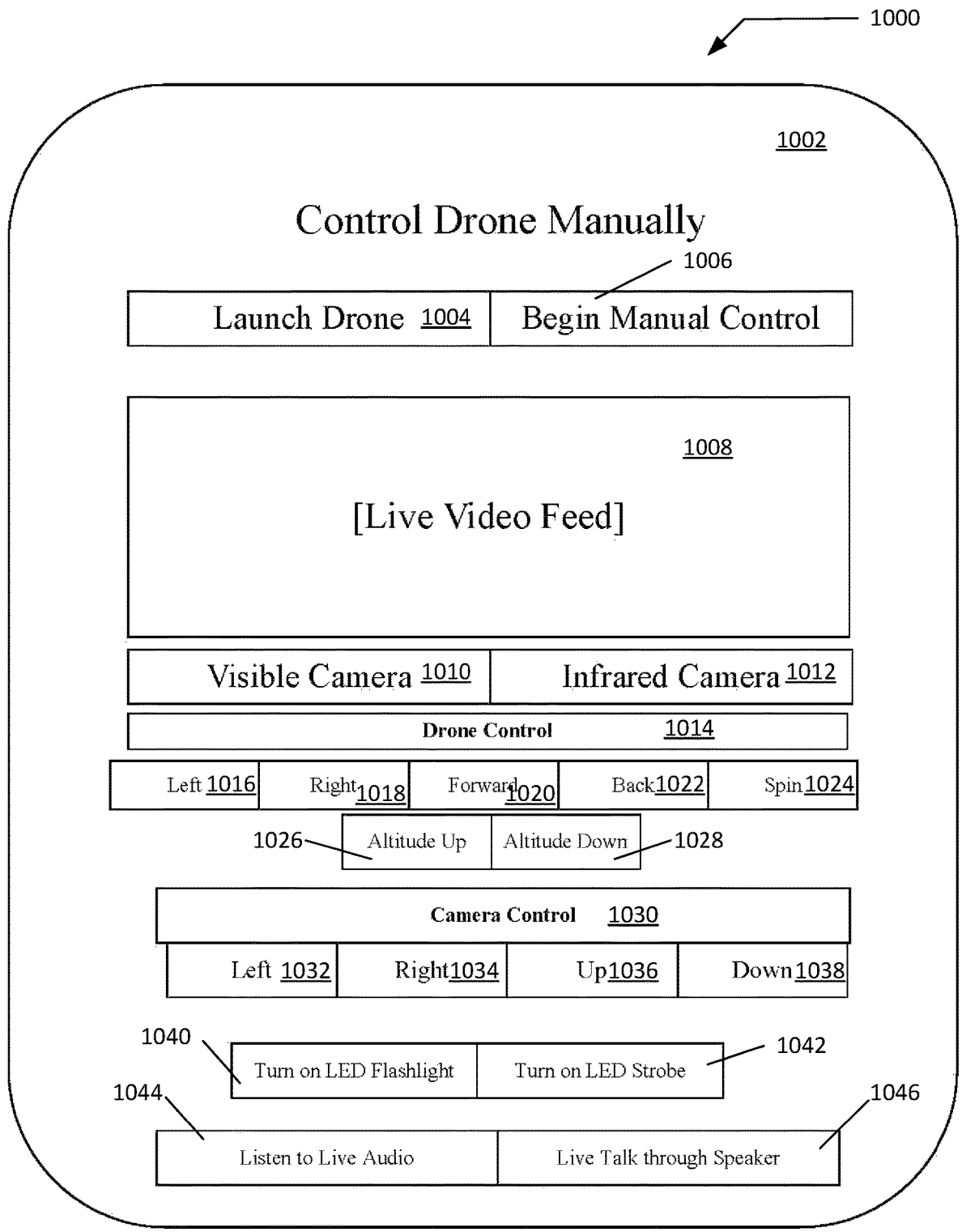
FIG. 10 illustrates a graphical user interface displayed on a smart device of FIG. 4 for control of the drone manually in accordance with an example implementation of the invention.

In FIG. 10, an illustration of a GUI 1002 displayed on a smart device 402 of FIG. 4 for control of the drone 102 manually is depicted in accordance with an example implementation of the invention. The drone 102 may be launched manually by selecting "Launch Drone 1004, if the drone 102 is not already flying. If the drone 102 is already flying, then manual control of the drone 102 may be asserted by selecting the "Begin Manual Control" button 1006. A view of a live video feed 1008 is also provided in GUI 1002 selectable from the available cameras on drone 102 (visible Camera 1010 and infrared Camera 1012). The manual controls of the drone 1014 include being able to manually move the drone left 1016, right 1018, forward 1020, back 1022, spin 1024, altitude up 1026 and altitude down 1028.

Similarly, manual control may be asserted over the camera with the camera control 1020 in GUI 1002. The selected camera, if on a gimbal or other movable device (electrically or optically) may be moved left 1032, right 1034, up 1036, and down 1038. Furthermore, an LED Flashlight 1040 or other light may be lite or made to strobe 1042. A microphone may be activated providing live audio to the smart device 402 by selecting the "Listen to Live Audio" button 1044. A speaker may be activated on the drone 102 by selecting the "Live talk through Speaker" button enabling streaming audio to be sent and played at the drone 102.

Once setup of the drone security system is complete and the drone base 202 is connected to the internet or other network, security access panel, burglar, fire, or access control system, a user must personally set the preferred default security settings for the drone 102 and drone base 202 actions. These default settings include the alarm sound that is played through the drone base 202 speakers 224, the alarm sound or pre-recorded message that is played through drone 102 speakers 120, the secondary landing location of drone 102, drone 102 actions in response to suspicious objects (including following the object while the object remains in geo fence), drone 102 action in response to detected heat or motion activity near the drone base 202, time or frequency of drone flight patterns, the GPS coordinates and altitude of drone flight path, and drone action in response to building burglar, fire, or access control alarms using the different GUIs.

The user interacts with a mobile app on smart device 402, web page, or a PC connected directly to the drone base 202. The user sees real-time data from the drone base 202 sensors 204 and monitoring capabilities. The user is able to see real-time data from drone 102 camera 110, microphone 118, GPS 116, and sensors 124. The user at their smart device 402 or computer receives alerts from the drone base 202. The user chooses an action using their smart device or computer after receiving alert of suspicious object detection. The user can manually control the drone's 102 flight path, altitude, camera direction, speaker sounds, LED flashlight, and LED strobe light. The user can transmit live audio to drone 102 speakers 120. The user can also access DVR data from their smart device 402 or computer.

The drone 102 may operate using a preprogrammed flight path. Operation based upon a preprogrammed flight path is optional. The user can program the drone 102 to remain in the drone base 202 until an alert of one of the existing building security, fire, or access control system components occurs. The drone base 202 connects to all existing building alarm systems. These systems send a notification to the drone base 202 that an alarm has been activated. Example alerts include motion sensors, cameras, windows, doors, gates, fire alarms, etc. Setup involves a GPS location for each component of the existing building alarm system. The drone 102 automatically leaves the drone base 202 and flies to the GPS coordinates of the security component alert. The drone 102 will send a notification to the smart device 402 or computer associated with the user that it is at the location. The drone 102 maintains its distance from the component while recording and transmitting live video and audio feeds of the component to the smart device 402 or computer of the user. The drone 102 can continue to transmit information to these feeds until it receives a command to stop the transmissions. The user can command the drone 102 to turn on its strobe lights or an alarm sound using the smart device 401. If the drone 102 runs low on battery it will automatically return to the drone base 202 or an alternate drone base to recharge.

The drone 102 is optionally programmed to follow a predetermined flight path to perform security and surveillance tasks. This flight path may be along the perimeter of a building or property and other "areas of interest." This may include entry ways or storage locations.

The drone 102 is configured to aim its camera's 110 at these "areas of interest" while the drone 102 travels along its predetermined flight path. Multiple cameras may be employed on drone 102 and target both the area of interest and get a 360 degree view. There may be multiple "areas of interest" along the drone's predetermined flight path. The camera controller that controls the direction of the camera 110 will automatically point in the direction of the "area of interest" until the drone 102 determines if there is any suspicious activity in the area of interest before aiming at a different area of interest. The drone 102 may be configured to know when specific areas should be unoccupied at specific times. The drone 102 can also know exceptions for activities like trash pickup times. The drone control unit 104 coordinates between the GPS location of the drone 102 and the GPS location of the specific object to keep the specific camera pointed at while the drone 102 continues moving along its predetermined flight path.

The predetermined flight path may be interrupted. If the camera detects movement heat signatures in areas of interest, the drone 102 changes its flight path to keep recording the source of movement or heat. A notification is sent to the smart device 402 or computer associated with the end user who can access the live video and audio feeds on the computer or smart device 402, or command the drone 102 to continue along its predetermined flight path in the case of a false alarm.

The drone 102 may issue a laser to determine the distance to the source object. The drone 102 remains a predetermined distance from the source object. The drone 102 automatically follows the object while avoiding hazardous objects. Hazardous objects are configured at set up so the drone 102 automatically avoids them. The drone 102 also avoids hazardous objects automatically using sensors.

The drone 102 follows the object while maintaining altitude and distance from the object and while the object remains within the geo fence. The geo fence is a specified boundary that is defined during set up. The drone 102 will not fly outside the geo fence and alerts or other alarms will be initiated if the drone 102 does move outside the geo fence.

If the source of movement or heat travels outside the geo fence, the drone 102 will stop at the geo fence and continue to record the video and audio of the source. When the camera 110 can no longer detect the source, the drone 102 begins a "security alert scan" in the current implementation. The drone 102 will not return to its predetermined flight path and instead fly in a pattern around the area that the original source left the geo fence in order to detect any additional sources of movement or heat.

The drone 102 can be setup to perform security alert scans for a specified period of time before returning to a predetermined flight path or continue performing security alert scans until it receives a command from the end user or runs low on battery power. Whenever the drone 102 observes a new source it alerts the user and follows the source.

The user can command the drone 102 to perform additional security alert scans or to return to one or more predetermined flight paths. The user may also toggle two-way communication so that voice audio can be sent and received through the drone. At any time the batteries run low, the drone automatically returns to base to recharge.

The drone 102 may also be set up to play an alert sound and/or flash LED strobe lights automatically when it detects a source. The drone 102 is also able to track objects moving toward it. The drone 102 produces "rapid evasive maneuvers" to dodge or fly out of the way of incoming objects. If signal with the drone 102 is lost, the drone base 202 notifies the end user. If the altimeter shows rapid descent or is disabled entirely indicating a possible crash or that the drone 102 was hit with an object but still being powered by the batteries, the drone sends an alert to the drone base 102 and/or smart device 402 or computer associated with the user.

The drone 102 transmits the GPS coordinates of the motion/heat source in real-time which can be seen through the GUI of smart device 402. If the drone runs low on batteries and needs to return to drone base 202, the drone base 202 can command another drone stored in the drone base 202 to leave the drone base 202 and fly directly to the GPS coordinate of the alert detected by drone 102.

The user is able to manually take over flying the drone 102 using the computer or smart device 402. This could be for the purposes of maintenance or inspection. The drone 102 monitors the health of its hardware. It sends a notification or alerts if something is not operational or failure is detected. The drone 102 may pause along its flight path for "manual inspection" of a specific "checkpoint" location. The drone 102 will send a notification to the user that it is at a "checkpoint" location. The drone will aim its camera 110 at the checkpoint location and wait for instructions from the user. The user can inspect the live camera and audio feed on a smart device 402 before commanding the drone 102 to continue its path. The drone 102 can be programmed to wait in this location for a specific period of time. If no command to resume is received, it can automatically resume its predetermined flight path.

Figure 11:
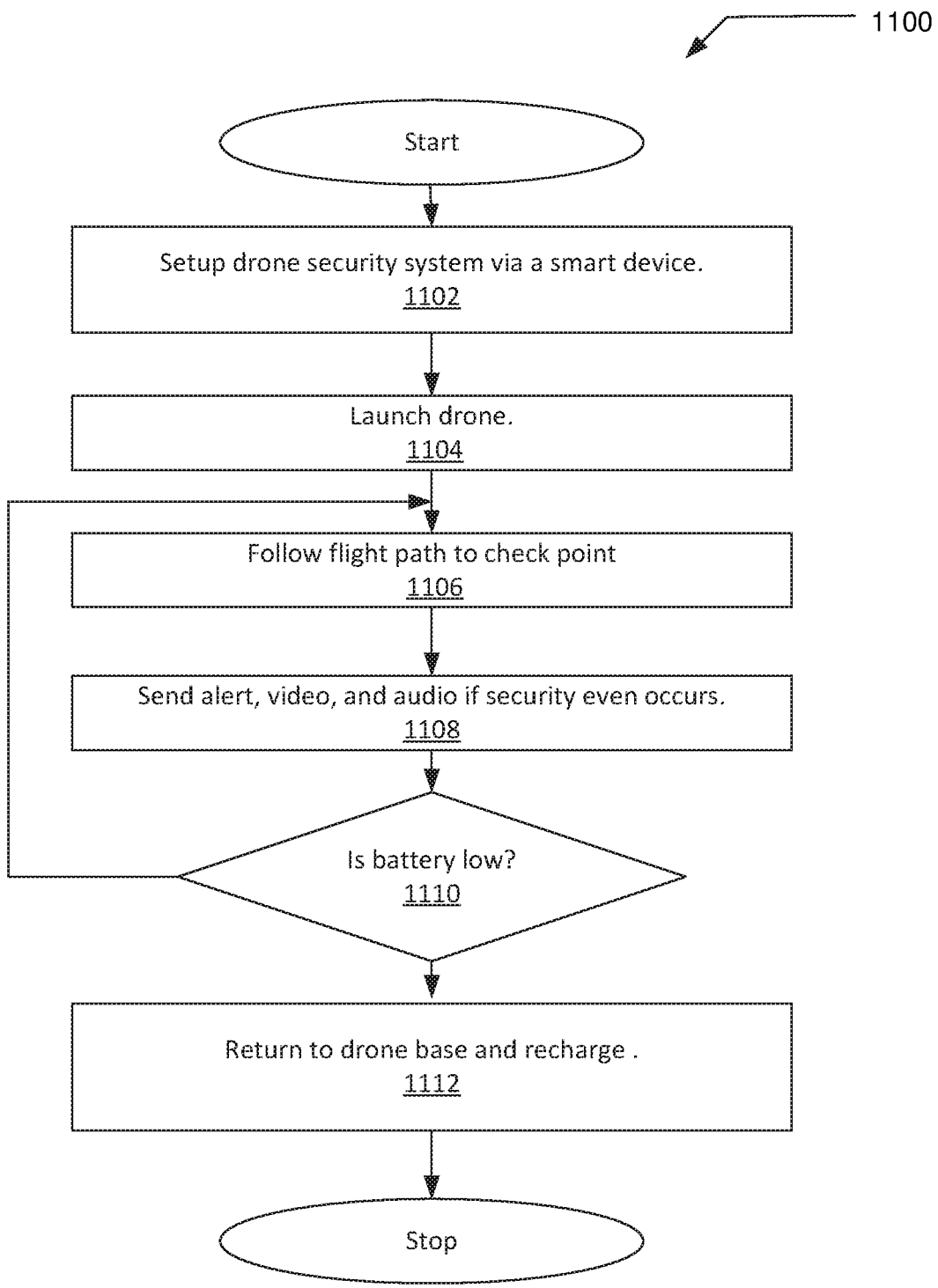
FIG. 11 illustrates a block diagram of the approach of operation of a security drone in accordance with an example implementation of the invention.

Turning to FIG. 11, an illustration of a block diagram 1100 of the approach of operation of a drone 102 in a security system is depicted in accordance with an example implementation of the invention. The approach starts with the drone security system (drone 102 and drone base 202) being setup using a computer or smart device 401 as previously explained in step 1102. The drone 102 is launched from the drone base 202 to fly a predetermined path in step 1104. The flight path is followed to check points in step 1106. If an event occurs at a check point or along the path, an alert, video and audio is transmitted from the drone 102 to the smart device 402 or computer either directly or via the drone base 202 in step 1108. Once the battery is low in the power unit 106 of drone 102 in step 1110, it returns to the drone base 202 and is recharged in step 1112. Otherwise it continues along the path and on to check points in step 1106.

It will be understood, and is appreciated by persons skilled in the art, that one or more processes, sub-processes, or process steps described above may be performed by hardware and/or software. If the process is performed by software, the software may reside in software memory (not shown) in a suitable electronic processing component or system such as, one or more of the functional components or modules schematically depicted in FIGS. 1-5. The software in software memory may include an ordered listing of executable instructions for implementing logical functions (that is, "logic" that may be implemented either in digital form such as digital circuitry or source code or in analog form such as analog circuitry or an analog source such an analog electrical, sound or video signal), and may selectively be embodied in any computer-readable medium for use by or in connection with an instruction execution system, apparatus, or device, such as a computer-based system, processor-containing system, or other system that may selectively fetch the instructions from the instruction execution system, apparatus, or device and execute the instructions. In the context of this disclosure, a "computer readable medium" is any means that may contain, store or communicate the program for use by or in connection with the instruction execution system, apparatus, or device. The computer readable medium may selectively be, for example, but is not limited to, an electronic, magnetic, optical, electromagnetic, infrared, or semiconductor system, apparatus or device. More specific examples, but nonetheless a non-exhaustive list, of computer-readable media would include the following: a portable computer diskette (magnetic), a RAM (electronic), a read-only memory "ROM" (electronic), an erasable programmable read-only memory (EPROM or Flash memory) (electronic) and a portable compact disc read-only memory "CDROM" (optical). Note that the computer-readable medium may even be paper or another suitable medium upon which the program is printed, as the program can be electronically captured, via for instance optical scanning of the paper or other medium, then compiled, interpreted or otherwise processed in a suitable manner if necessary, and then stored in a computer memory.

It will be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

The foregoing description of an implementation has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

The invention claimed is:

1. A drone security system, comprising:
    a security system;
    a drone; and
    a drone base configured to communicate with the drone and automatically dispatch the drone in response to a location of an event in the security system and transmits at least a video with at least one camera from the location of the event with a radio module that transmits the at least video to a digital video recorder (DVR) that is viewable at a location associated with a traditional alarm system and where the drone returns to the drone base when a predetermined power level is detected.

2. The drone security system of claim 1, where the drone operates within a geo fenced area.

3. The drone security system of claim 1, where the drone has at least one camera that is facing the location of the event as the drone approaches the event.

4. The drone security system of claim 1, where a manual control is asserted over the drone once the drone is at the location of the event.

5. The drone security system of claim 1, where the drone transmits the at least video via the drone base.

6. The drone security system of claim 1, where a smart device receives the at least video.

7. A drone security system with a drone, comprising:
a memory;
a navigation unit;
a radio module;
a motor control unit;
a camera;
a power unit adapted to connect the drone to a drone base;
a microphone;
a speaker;
a controller unit coupled to a processor, the speaker, the microphone, the power unit, the radio module, the navigation unit, where the controller receives a predetermined flight path via the radio module and executes the predetermined flight path at a predetermined time, where the drone was automatically dispatched and returns automatically to the drone base when a predetermined power level is detected; and
a video image captured by the camera transmitted by the radio module to a digital video recorder (DVR) located that is located at a location associated with a traditional alarm system.

8. The drone security system with the drone of claim 7, where the radio module sends an alert if an event at a location occurs while following the predetermined flight path.

9. The drone security system with the drone of claim 8, where the event results in the drone waiting at the location for manual control for a predetermined time period.

10. The drone security system with the drone of claim 9, the camera is directed towards a check point along the predetermined path as the drone approaches that check point.

11. The drone security system with the drone of claim 8, where a camera captures a video image and transmits it via the radio module.

12. The drone security system with the drone of claim 8, where a second camera is activated in response to receiving a signal via the radio module.

13. The drone security system with the drone of claim 8, where the drone returns to a drone base in response to the power unit needing to be recharged.

14. A drone security system method, comprising:
configuring a drone base with location information associated with a traditional alarm system;
defining for a drone at least one flight path with one or more check points along the flight path;
sending the drone from the drone base along a predetermined flight path automatically;
rerouting the drone to a location associated with a traditional alarm system in response to the drone base receiving a notification from the traditional alarm system;
transmitting from a radio module located on the drone;
generating video from a camera located on the drone that transmits the video via a radio module to a digital video recorder (DVR) located at the location associated with the traditional alarm system; and
returning the drone to the drone base when a predetermined power level is detected.

15. The drone security system method of claim 14, where sending the drone further includes sending the drone at a predetermined time along the predetermined flight path.

16. The drone security system method of claim 14, where the drone security system includes limiting operations of the drone within a geo fenced area.

17. The drone security system method of claim 14, where the drone security system includes directing the camera at the location as the drone approaches the location.

18. The drone security system method of claim 14, where the drone security system includes asserting manual control over the drone once the drone at the location.

* * * * *